United States Patent
Melman

(10) Patent No.: US 9,968,313 B2
(45) Date of Patent: *May 15, 2018

(54) X-RAY TUBE

(71) Applicant: ControlRad Systems Inc., Radnor, PA (US)

(72) Inventor: Haim Zvi Melman, Kfar Saba (IL)

(73) Assignee: CONTROL RAD SYSTEMS INC, Radnor, PA (US)

(*) Notice: Subject to any disclaimer, the term of this patent is extended or adjusted under 35 U.S.C. 154(b) by 901 days.

This patent is subject to a terminal disclaimer.

(21) Appl. No.: 14/370,968

(22) PCT Filed: Jan. 7, 2013

(86) PCT No.: PCT/IB2013/050129
§ 371 (c)(1),
(2) Date: Jul. 8, 2014

(87) PCT Pub. No.: WO2013/105011
PCT Pub. Date: Jul. 18, 2013

(65) Prior Publication Data
US 2015/0016589 A1 Jan. 15, 2015

Related U.S. Application Data

(60) Provisional application No. 61/585,249, filed on Jan. 11, 2012.

(51) Int. Cl.
*A61B 6/06* (2006.01)
*A61B 6/00* (2006.01)
(Continued)

(52) U.S. Cl.
CPC .............. *A61B 6/4021* (2013.01); *A61B 6/06* (2013.01); *A61B 6/467* (2013.01); *A61B 6/487* (2013.01);
(Continued)

(58) Field of Classification Search
CPC .. H01J 35/14; H01J 35/08; H01J 35/06; H01J 2235/186; H01J 35/30; H01J 35/10; H01J 2235/068; H01J 2235/1204; H01J 35/02; H01J 35/305; H01J 35/045; H01J 35/04; H01J 35/24; H01J 1/304
See application file for complete search history.

(56) References Cited

U.S. PATENT DOCUMENTS 4,998,270 A 3/1991 Scheid et al.
5,091,926 A 2/1992 Horton et al.
(Continued)

FOREIGN PATENT DOCUMENTS

EP 0476185 A1 3/1992

*Primary Examiner* — Hoon Song

(57) ABSTRACT

A fluoroscopic system is disclosed with capability of differential exposure of different input areas of an image intensifier. The x-ray beam solid angle is limited by a collimator that is relatively near to the focal point of the x-ray tube, to occupy an area smaller then the input area of the image intensifier. Means to deflect the electron beam of the x-ray tube in two dimensions are constructed with the x-ray tube to provide scanning capability of the complete input area with full control on the motion function. The collimator may also be moved to control beam size and/or position at the image intensifier.

23 Claims, 9 Drawing Sheets

(51) Int. Cl.
*H01J 35/14* (2006.01)
*G21K 1/02* (2006.01)
*G21K 1/04* (2006.01)

(52) U.S. Cl.
CPC ............ *A61B 6/5211* (2013.01); *A61B 6/542* (2013.01); *G21K 1/02* (2013.01); *H01J 35/14* (2013.01); *G21K 1/04* (2013.01)

(56) References Cited

U.S. PATENT DOCUMENTS

| | | | |
|---|---|---|---|
| 5,282,254 A | 1/1994 | Chiu et al. | |
| 9,517,041 B2 * | 12/2016 | Melman | A61B 6/06 |
| 2010/0111261 A1 | 5/2010 | Maack | |
| 2010/0303202 A1 | 12/2010 | Ren et al. | |
| 2011/0051895 A1 * | 3/2011 | Vogtmeier | A61B 6/032 |
| | | | 378/92 |
| 2011/0058653 A1 * | 3/2011 | Baumgart | G06T 19/00 |
| | | | 378/98.2 |
| 2011/0150187 A1 | 6/2011 | Boudry et al. | |
| 2011/0170665 A1 | 7/2011 | Gertner | |

* cited by examiner

X-RAY TUBE

FIELD OF THE INVENTION

The invention is related to the field of x-ray tubes and more particularly to the field of creating and controlling x-ray radiation geometry.

BACKGROUND OF THE INVENTION

Typical x-ray tubes generate x-ray radiation over a relatively wide solid angle. To avoid unnecessary exposure to both the patient and the medical team, collimators of x-ray absorbing materials such as lead are used to block the redundant radiation. This way only the necessary solid angle of useful radiation exits the x-ray tube to expose only the necessary elements.

Such collimators may assume a variety of designs and x-ray radiation geometry. Collimators can be set up manually or automatically using as input, for example, the dimensions of the cassette holding the plate to limit the radiation to the dimensions of the film in the cassette.

In fluoroscopy the situation is more dynamic than in a single exposure x-ray. The x-ray radiation is active for long periods and the treating physician typically has to stand near the patient, therefore near the x-ray radiation. As a result, it is desired to provide methods to minimize exposure to the medical team. Methods for reducing x-ray radiation intensity have been suggested where the resultant reduced signal to noise ratio (S/N) of the x-ray image is compensated by real-time digital image enhancement. Other methods suggest a collimator limiting the solid angle of the x-ray radiation to a fraction of the image intensifier area and moving the collimator to sweep the entire input area of the image intensifier where the Region of Interest (ROI) is exposed more than the rest of the area. This way, the ROI gets high enough x-ray radiation to generate a good S/N image while the rest of the image is exposed with low x-ray intensity, providing a relatively low S/N image. The ROI size and position can be determined in a plurality of methods. For example, it can be a fixed area in the center of the image or it can be centered automatically about the most active area in the image, this activity is determined by temporal image analysis of a sequence of cine images received from the video camera of the fluoroscopic system.

Reference is made now to FIG. 1A which presents a typical layout of a fluoroscopy clinical environment.

X-ray tube 100 generates x-ray radiation 102 directed upward occupying a relatively large solid angle towards collimator 104. Collimator 104 blocks a part of the radiation allowing a smaller solid angle of radiation to continue in the upward direction, go through bed 108 that is typically made of material that is relatively transparent to x-ray radiation and through patient 110 who is lying on bed 108. Part of the radiation is absorbed and scattered by the patient and the remaining radiation arrives at the typically round input area 112 of image intensifier 114. The input area of the image intensifier is typically in the order of 300 mm in diameter but may vary per the model and the technology. The image generated by image intensifier 114 is captured by video camera 116 and then displayed on monitor 118 as image 120.

In modern systems the image intensifier and video camera are often replaced by a rectangle flat panel detector. It would be appreciated that the description below referring to image intensifiers and video cameras is analog for the case of a flat panel detector or other detectors converting x-ray radiation to an electronic image.

Operator 122 is standing by the patient to perform the medical procedure while watching image 120.

The operator has a foot-switch 124. When pressing the switch, continuous x-ray radiation is emitted to provide cine imaging 120. The intensity of x-ray radiation is typically optimized in a tradeoff of low x-ray intensity that is desired to reduce exposure to the patient and the operator and high x-ray intensity that is desired to enable a high quality image 120 (high S/N). With low intensity x-ray radiation and thus low exposure of the image intensifier input area, the S/N of image 120 might be so low that image 120 becomes useless.

SUMMARY OF THE INVENTION

According to a first aspect of the present invention there is provided an x-ray tube assembly comprising a cathode, an anode; and means for controlling collision location of electrons emitted from the cathode on the anode.

The means may comprise at least one electromagnetic device connected to a current source; wherein a current level is selected to generate a desired magnetic field in a path of the electrons flowing from said cathode to said anode.

The at least one electromagnetic device may comprise two electromagnetic devices configured to produce magnetic fields in the path of the electrons flowing from said cathode to said anode, said magnetic fields generally perpendicular to each other.

The current in each of the electromagnetic devices may be set to determine the collision location of the electrons emitted from the cathode on the anode.

The x-ray tube assembly may further comprise a collimator forming an aperture limiting a solid angle of an x-ray beam emitted from the x-ray tube.

The current in each of the electromagnetic devices may be set to determine a direction of said solid angle of the x-ray beam.

The aperture may be movable in a plane generally parallel to a surface of the collimator.

A direction of said solid angle may be determined by a combination of the current in each of the electromagnetic devices and a location of said movable aperture. Only one electromagnetic device may be used; and the direction of said solid angle may determined by a combination of the current in said electromagnetic device and the location of said movable aperture.

The means for controlling collision location of electrons emitted from the cathode on the anode may comprise at least one device for generating an electric field, said device connected to an electric potentials source, wherein electric potential levels are controllable to generate a desired electric field in a path of the electrons flowing from said cathode to said anode.

The at least one device may comprise two devices configured to produce electric fields in the path of the electrons flowing from said cathode to said anode, said electric fields generally perpendicular to each other.

The electric potential applied to each of the devices may be set to determine a collision location of the electrons emitted from the cathode on the anode.

The x-ray tube assembly may further comprise a collimator forming an aperture limiting a solid angle of an x-ray beam emitted from the x-ray tube.

The electric potential applied to each of the devices may be set to determine a direction of said solid angle of the x-ray beam.

The aperture may be movable in a plane generally parallel to a surface of the collimator.

A direction of said solid angle may be determined by a combination of the electric potential applied to each of said devices and a location of said movable aperture. Only one of said devices may be used and the direction of said solid angle may be determined by a combination of the electric potential applied to said device and the location of said movable aperture.

The collimator may be movable in a plane generally perpendicular to a surface of the collimator.

According to a second aspect of the present invention there is provided an x-ray system comprising; an x-ray tube assembly; an image detector; a monitor configured to display detected images; means for determining the location of a Region of Interest (ROI) of an operator on said displayed image; a first controller connected with said means for determining; an image processing unit connected with said image detector, said monitor and said first controller, said image processing unit configured to optimize the detected image displayed on said monitor according to the image part in said ROI; and a second controller connected with said x-ray tube assembly, said second controller configured to control operating parameters of said x-ray tube, wherein said x-ray tube assembly comprises a cathode, an anode; and means for controlling collision location of electrons emitted from the cathode on the anode.

The means for determining the location of a ROI may comprise an eye tracker. The first controller may be further configured to calculate a collision location of electrons emitted from the cathode on the anode according to said determined location of the ROI.

The means for determining collision location may comprise at least on electromagnetic device connected to a current source; wherein a current level may be selected to generate a desired magnetic field in the path of electrons flowing from said cathode to said anode.

The at least one electromagnetic device may comprises two electromagnetic devices configured to produce magnetic fields in the path of electrons flowing from said cathode to said anode, said magnetic fields generally perpendicular to each other.

A current in each of the electromagnetic devices may be set to determine a collision location of the electrons emitted from the cathode on the anode.

The x-ray system may further comprise a collimator forming an aperture limiting a solid angle of an x-ray beam emitted from the x-ray tube.

The current in each of the electromagnetic devices may be set to control a direction of said solid angle of the x-ray beam.

The aperture may be movable in a plane generally parallel to a surface of the collimator.

A direction of said solid angle may be determined by a combination of the current in each of the electromagnetic devices and the location of said movable aperture. The first controller may be further configured to calculate a location and size of said collimator aperture according to said determined location of the ROI.

Only one electromagnetic device may be used; and the direction of said solid angle may be determined by a combination of the current in said electromagnetic device and the location of said movable aperture.

The means for controlling a collision location may comprise at least one device for generating an electric field, said device connected to an electric potentials source, wherein electric potential levels may be determined to generate a desired electric field in the path of electrons flowing from said cathode to said anode.

The at least one device may comprise two devices configured to produce electric fields in the path of the electrons flowing from said cathode to said anode, said electric fields generally perpendicular to each other.

The electric potential applied to each of the said devices may be set to determine a collision location of electrons emitted from the cathode on the anode.

The x-ray system may further comprise a collimator forming an aperture limiting a solid angle of an x-ray beam emitted from the x-ray tube.

An electric potential applied to each of the devices may be set to determine the direction of said solid angle of the x-ray beam.

The aperture may be movable in a plane generally parallel to a surface of the collimator.

The direction of said solid angle may be determined by a combination of the electric potential applied to each of said devices and a location of said movable aperture.

Only one of said devices may used and the direction of said solid angle may be determined by a combination of the electric potential applied to said device and the location of said movable aperture.

The collimator may be movable in a plane generally perpendicular to a surface of the collimator.

The first controller may be further configured to calculate a location and size of said collimator aperture according to said determined location of the ROI.

The direction of said solid angle may be determined by a combination of the current in each of the electromagnetic devices and a location of said aperture. According to a third aspect of the present invention there is provided a method of controlling collision location of electrons emitted from a cathode on an anode in an x-ray tube assembly, comprising: providing at least one electromagnetic device in a path of said electrons flowing from said cathode to said anode; connecting said at least one electromagnetic device to a current source; and selecting a current level to generate a desired magnetic field in said path of the electrons flowing from said cathode to said anode.

The at least one electromagnetic device may comprise two electromagnetic devices configured to produce magnetic fields in the path of the electrons flowing from said cathode to said anode, said magnetic fields generally perpendicular to each other.

A current in each of the electromagnetic devices may be set to determine the collision location of the electrons emitted from the cathode on the anode.

The method may further comprise: providing a collimator forming an aperture limiting a solid angle of an x-ray beam emitted from the x-ray tube; and setting the current in each of the electromagnetic devices to determine a direction of said solid angle of the x-ray beam.

The aperture may be movable in a plane generally parallel to a surface of the collimator.

The direction of the solid angle may be set by a combination of the current in each of the electromagnetic devices and a location of said movable aperture.

The method may comprising using only one electromagnetic device, wherein the direction of said solid angle may be set by a combination of the current in said electromagnetic device and the location of said movable aperture.

According to a fourth aspect of the present invention there is provided a method of controlling collision location of electrons emitted from a cathode on an anode in an x-ray tube assembly, comprising: providing at least one device for generating an electric field; connecting said device to an electric potentials source; and controlling electric potential levels to generate a desired electric field in a path of the electrons flowing from said cathode to said anode.

The at least one device may comprise two devices configured to produce electric fields in the path of the electrons flowing from said cathode to said anode, said electric fields generally perpendicular to each other.

The electric potential applied to each of the said devices may be set to determine a collision location of the electrons emitted from the cathode on the anode.

The method may further comprise: providing a collimator forming an aperture limiting a solid angle of an x-ray beam emitted from the x-ray tube; and setting the electric potential applied to each of the devices to determine a direction of said solid angle of the x-ray beam.

The aperture may be movable in a plane generally parallel to a surface of the collimator.

A direction of said solid angle may be determined by a combination of the electric potential applied to each of said devices and a location of said movable aperture. Only one of said devices is used and the direction of said solid angle may be determined by a combination of the electric potential applied to said device and the location of said movable aperture.

BRIEF DESCRIPTION OF THE DRAWINGS

The invention will be better understood in reference to the following Figures:

FIG. 6 illustrates an x-ray tube where the electron beam can be deflected in one direction and the collimator in another direction; and.

DETAILED DESCRIPTION OF THE INVENTION

Figure 1A:
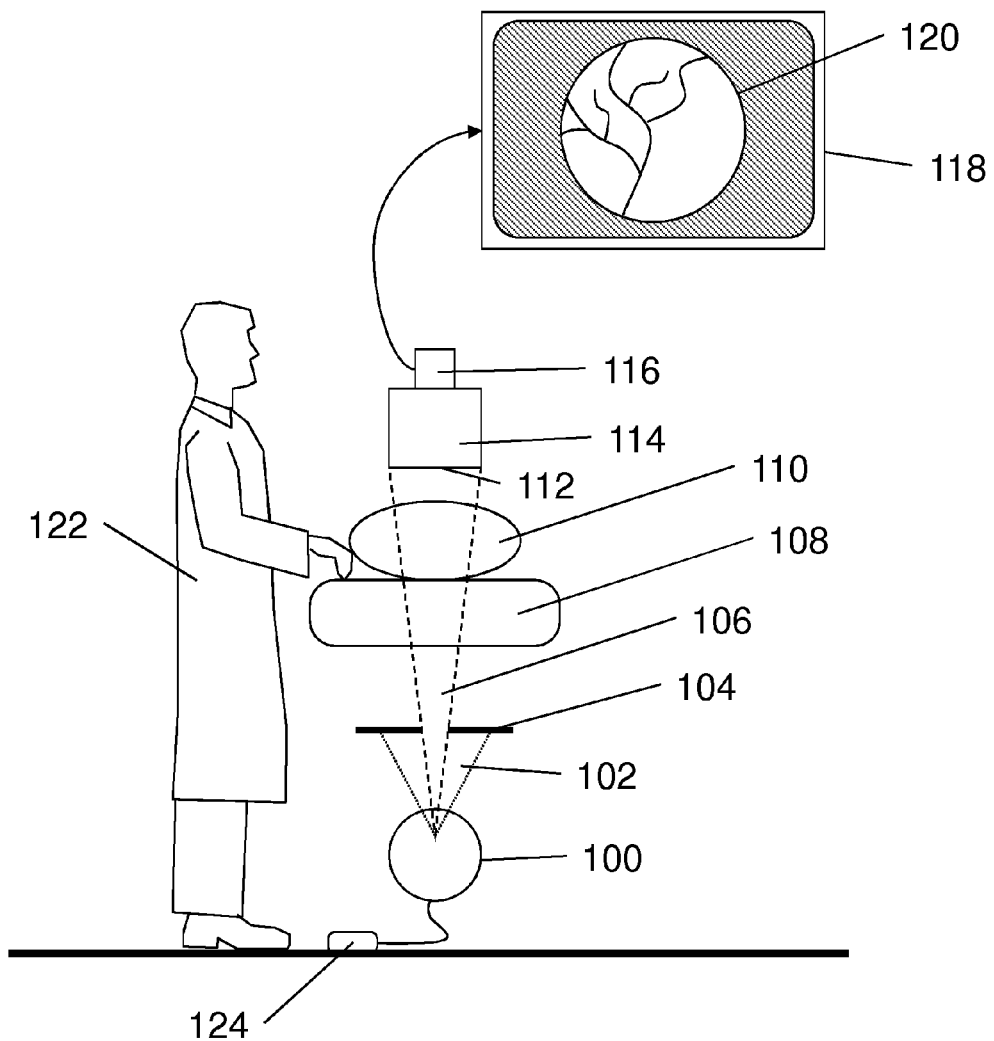
FIG. 1A is a schematic drawing of a typical layout of a fluoroscopy clinical environment.
Figure 1B:
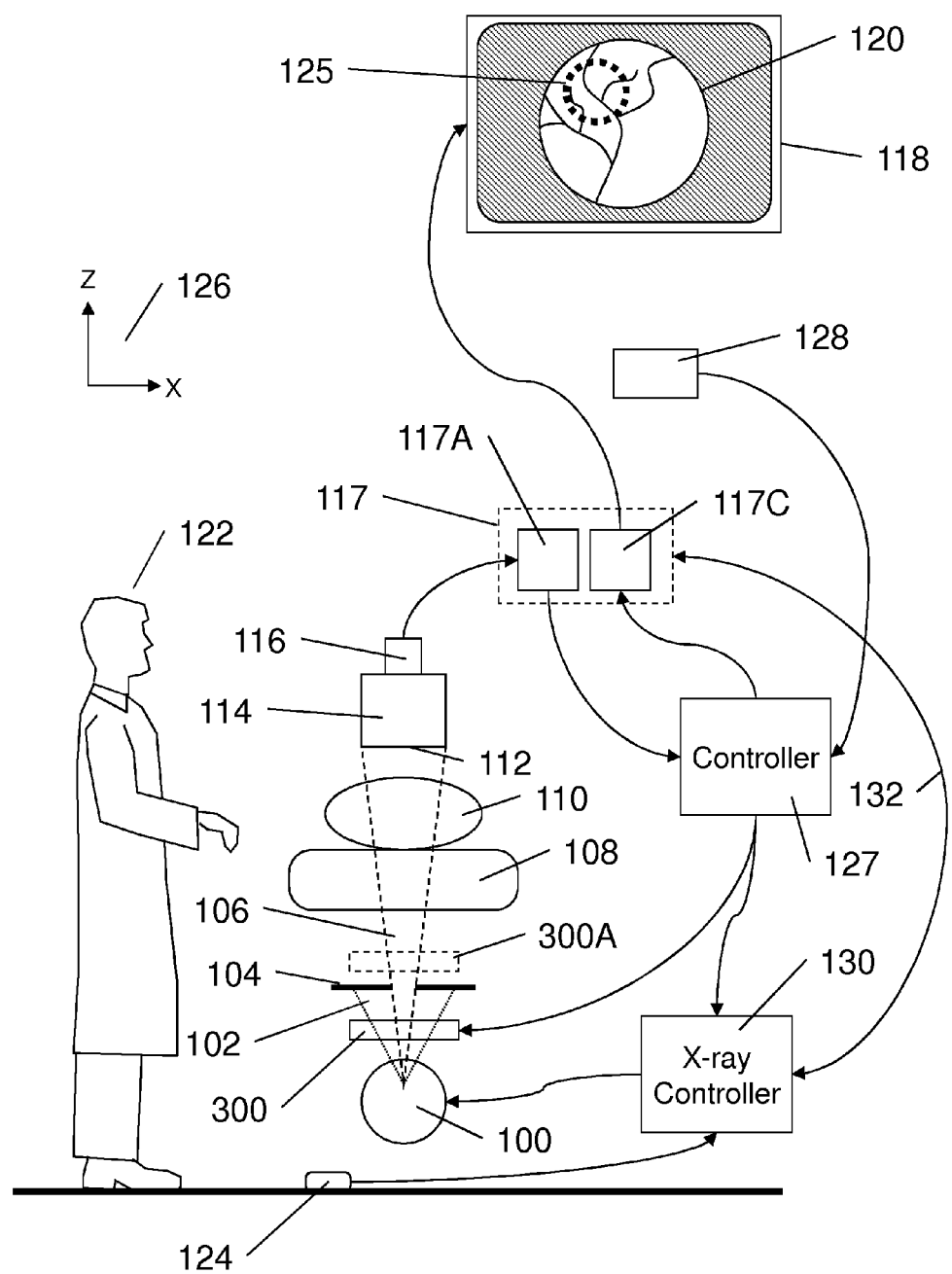
FIG. 1B is an illustration of an example of a layout of the system of FIG. 1A showing additional details of components of the system example of the invention.

The present invention provides means for attaining high exposure at the input area of the image intensifier in the desired Region of Interest (ROI) that will provide therefore a high S/N image there while reducing the exposure of other sections of the image intensifier area, at the cost of lower image quality (lower S/N). With this arrangement the operator can see a clear image in the ROI and get a good enough image for general orientation in the rest of the image area. ROI 125 location example in image area 120 as shown in FIG. 1B can be determined by any mean such as, but not limited to, pointing by a mouse at the desired center position of the ROI, using a track-ball to move ROI over image 120 area, typing-in image coordinates for ROI center, using input from an eye tracker to place the ROI at the gazing point of the user, etc.

One such example according to the present invention is presented hereinbelow in more details in reference to FIG. 1B.

Operator 122 presses foot switch 124 to activate x-ray. Eye tracker 128 (such as EyeLink 1000 available from SR Research Ltd., Kanata, Ontario, Canada) or any alternative input device provides indication where operator 122 is looking. This information is typically provided relative to monitor 118. This information, the "gazing point", may be provided for example in terms of (X,Z) coordinates, in the plane of monitor 118, using coordinate system 126. It would be appreciated that in this example the plane of monitor 118 and therefore also image 120 are parallel to the (X,Z) plane of coordinate system 126. Other coordinate systems are possible, including coordinate systems that are bundled to monitor 118 and rotate with monitor 118 when it is rotated relative to coordinate system 126. The data from input 128 is provided to controller 127 which is basically a computer, such as any PC computer. If the controller 127 determines that the operator's gaze is not fixed on the image 120, the x-ray tube 100 is not activated. Otherwise x-ray tube 100 is activated and x-ray radiation is emitted towards collimator 104 (and 300/300A if they are included in the system as will be explained in reference to FIGS. 3, 4, 6 and 7).

Box 300 can be located under collimator 104 or above collimator 104 as shown by numerical reference 300A. The collimators represented by boxes 300 and 300A are controlled by controller 127. X-ray emission is also controlled by controller 127, typically through x-ray controller 130. In one example, x-ray can be stopped even if operator 122 presses foot-switch 124, if the operator's gazing point is not within image 120 area. Also the location of focal point 304 (shown in FIG. 3) is controlled according to the location of ROI 125 through controller 127 as explained, for example, in reference to FIGS. 3 and 4. The collimator partially blocks radiation, depending on the determined operator's gazing point (or other ROI position input method) and thus part of the x-rays are absorbed by patient 110 and the remaining radiation arrives at image intensifier 114. The image is captured by a camera 116 and is transferred to image processor 117. Processed image 120 is displayed on monitor 118.

Image processor 117 may assume many forms and may be incorporated in the current invention in different ways. In the example of FIG. 1B, image processor 117 includes two main sub units: 117A provides basic image correction such as pixel non-uniformity (dark offset, sensitivity, reconstruction of dead pixels etc), 117C provides image enhancement processing (such as noise reduction, un-sharp masking, gamma correction etc). In conventional systems, the image from sub-unit 117A is transferred for further processing in sub-unit 117C. The sub-units of image processor 117 can be supported each by a dedicated hardware but they can also be logical sub-units that are supported by any hardware.

In the example of FIG. 1B the image from camera 116 is corrected by image processing sub-unit 117A and then transferred to controller 127. Controller 127 processes the image as required from using any of the collimators represented by box 300 and 300A and/or from moving focal point 304 (FIG. 3) to compensate for non-uniform exposure of image 120 area and returns the processed image to sub-unit 117C for image enhancement.

It can be appreciated that the image processing of controller 127 does not have to take place in controller 127 and it can be executed by a third sub-unit 117B (not shown in FIG. 1B) located between 117A and 117C. Sub-unit 117B can also be only a logical unit performed anywhere in image processor 117.

It would also be appreciated that x-ray controller 130 is presented here in the broad sense of system controller. As such it may also communicate with image processor 117 to determine its operating parameters and receive information as shown by communication line 132, It may control image intensifier 114, for example for zoom parameters (communication line not shown), it may control camera 116 parameters (communication line not shown), it may control the c-arm and bed position (communication line not shown) and it may control x-ray tube 100 and collimator 104 operation parameters (communication line not shown). There may be a user interface for operator 122 or other staff members to input requests or any other needs to x-ray controller 130 (not shown).

Physically, part or all of image processor 117, controller 127 and x-ray generator (the electrical unit that drives x-ray tube 100) may all be included in x-ray controller 130. X-ray controller 130 may contain one or more computers and suitable software to support the required functionality. An example for such a system with an x-ray controller is mobile c-arm OEC 9900 Elite available from GE OEC Medical Systems, Inc., Salt Lake City, Utah USA. It would be appreciated that the example system is not identical to the system of FIG. 1B and is only provided as a general example. Part of these features are shown in FIG. 26.

Figure 2A:
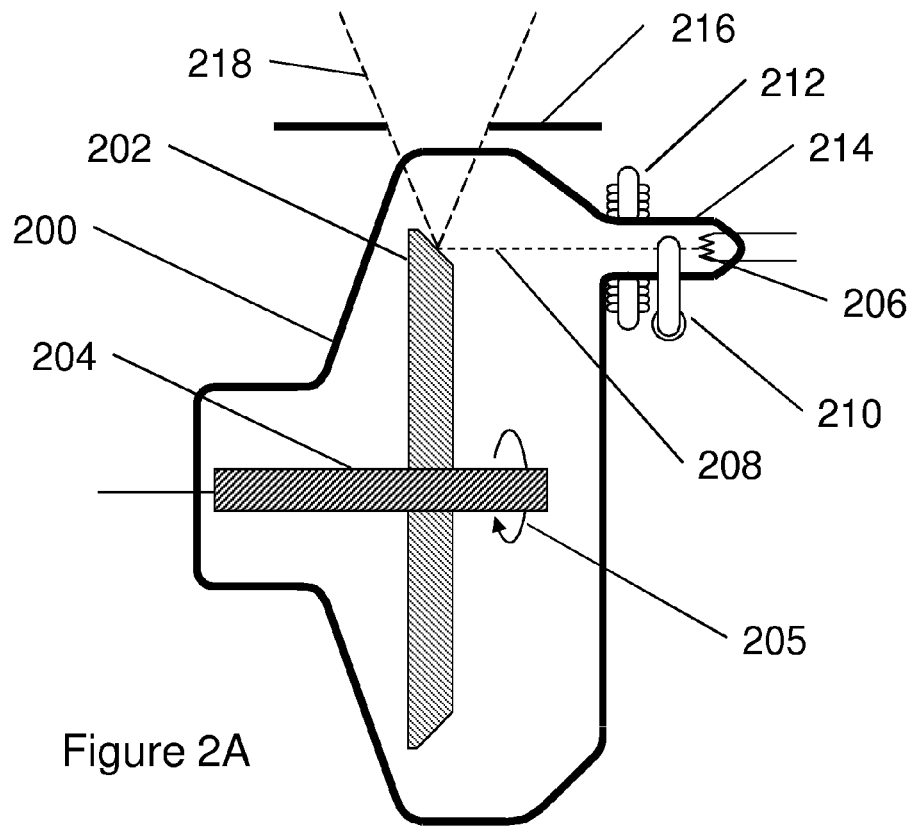
FIG. 2A illustrates a schematic x-ray tube with deflection yokes including ferromagnetic cores.

Reference is made now to FIG. 2A illustrating a schematic x-ray tube with deflection yokes comprising ferromagnetic cores.

Encapsulation 200 enables the vacuum required to enable electron beam 208. A cross section of anode 202 is shown. Anode 202 is a typical rotation anode that rotates about axis 204 (cross section is shown) as illustrated by arrow 205. Cathode 206 emits electron beam 208 that is focused on anode 202. Deflection yokes 210 and 212 are arranged generally perpendicular to each other on cylindrical section 214 of the x-ray tube encapsulation 200, as will be explained in more details in FIG. 2B. X-ray radiation resulting from the collision of the electrons of electron beam 208 with anode 202 is radiating in a relatively broad solid angle that is then limited by collimator 216 to produce the limited solid angle 218. The typical geometry, with a round collimator opening in the case of a round image intensifier input area, will produce a conical x-ray beam that spreads out towards the image intensifier. When reaching the image intensifier input area the diameter of the beam is generally the same as the diameter of the image intensifier input area. This enable the full utilization of the image intensifier input area but, at the same time, the ROI that may be in the order of 50 mm in diameter and the rest of input area 112 of FIG. 1A are exposed with a similar radiation regardless of the distinguishable value for the operator of the two sections.

Figure 2B:
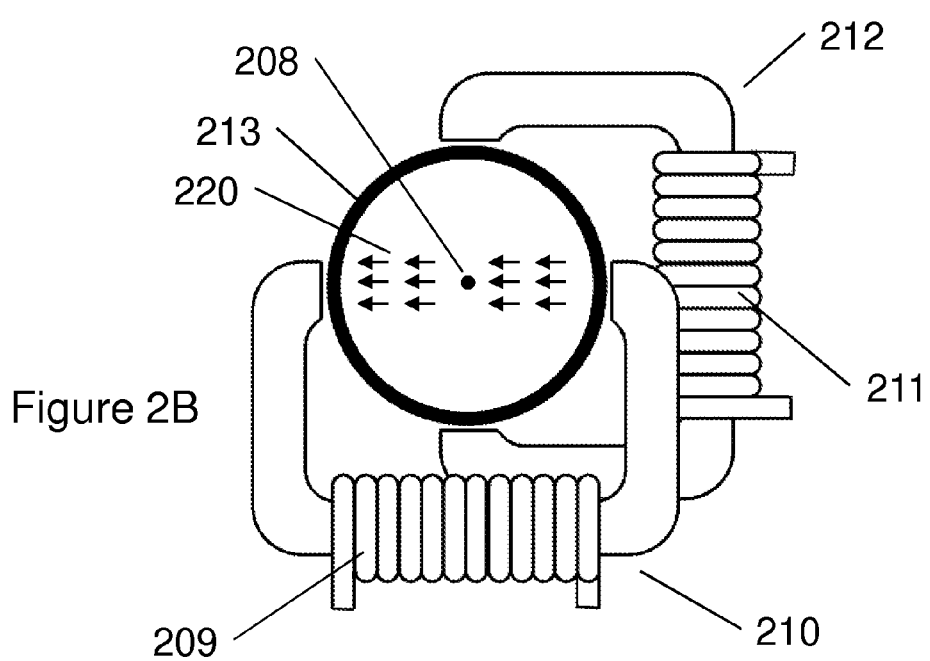
FIG. 2B illustrates a more detailed view of an arrangement of the deflection yokes of FIG. 2A.

Reference is made now to FIG. 2B illustrating the arrangement of yokes 210 and 212 in more details.

213 is a cross section of the cylindrical element of encapsulation 200 described in references to FIG. 2A. 208 is the electron beam of FIG. 2A shown in a cross section view of the electron beam. The electrons propagate into the page.

At rest, no current is driven through coil 209 of yoke 210 and coil 211 of yoke 212.

Now, if electrical DC current is introduced through coil 209, a horizontal magnetic field is generated in the space where the electrons of electron beam 208 are traveling. This is demonstrated by magnetic field arrows 220. As a result of magnetic field 220 the electrons in electron beam 208 sense electromagnetic force downwards and move in this direction. As a result, electron beam 208 will collide with the anode 202 at a lower point compared to the situation of no electrical current in coil 209. Similarly electron beam 208 can be deflected upwards by introducing to coil 209 an electrical current in the other direction. The amount of vertical deflection of electron beam 208 depends on the magnitude and the direction of the electrical current in coil 209.

In a similar way, by controlling the electrical current through coil 211 a vertical magnetic field can be manipulated to deflect electron beam 208 in the horizontal direction as desired.

Figure 2C:
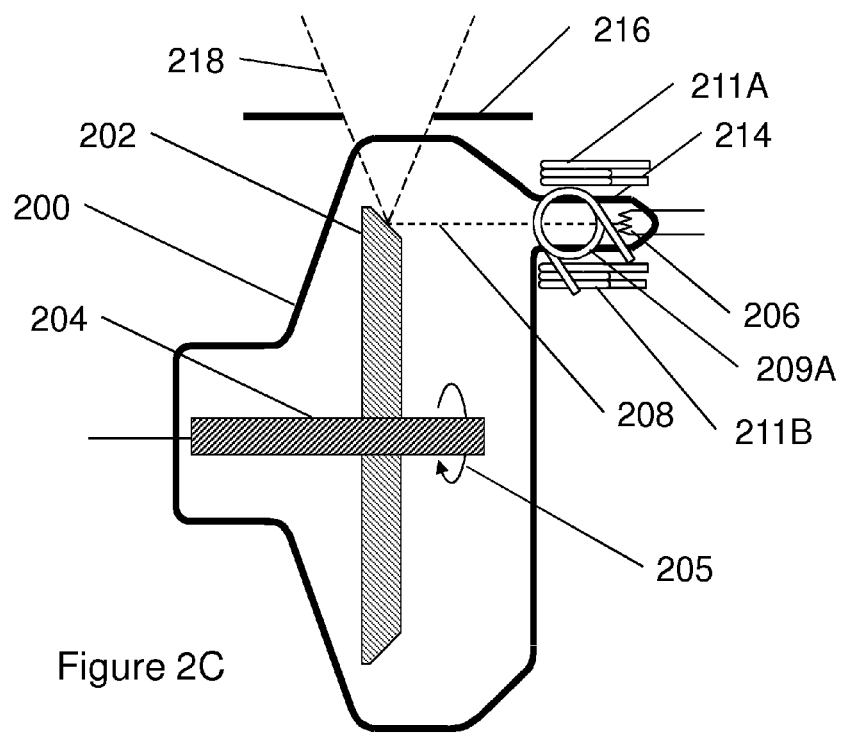
FIG. 2C illustrates a schematic x-ray tube with deflection coils only, without ferromagnetic cores.
Figure 2D:
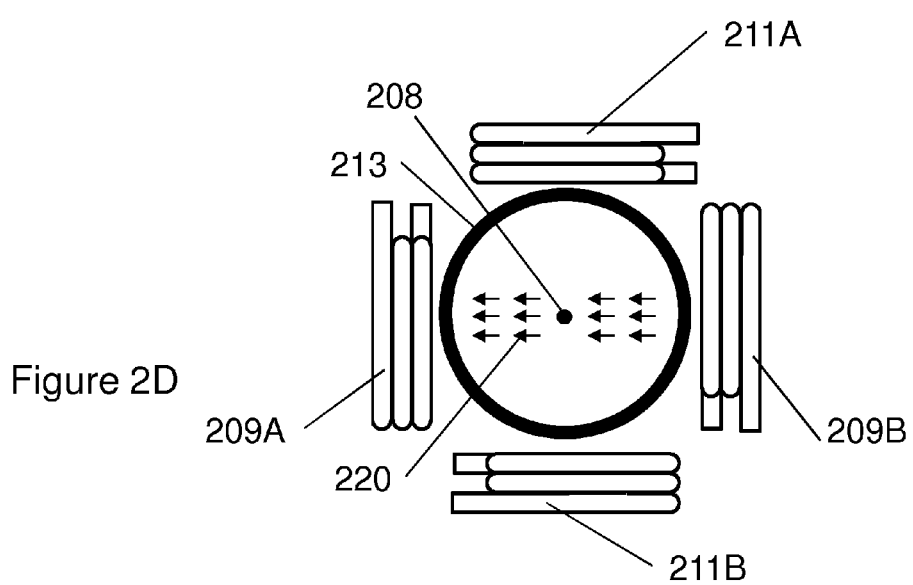
FIG. 2D illustrates a more detailed view of an arrangement of the deflection coils of FIG. 2C.

In FIGS. 2C and 2D the yokes are replaced with coils only (no ferromagnetic core is used). The coils are arranged so that electron beam 208 is parallel to the plane of the coils. In the example of FIG. 2D, when current is driven through coils 209A and 209B in one direction, a magnetic field 220 is created and thus, electron beam 208 passing perpendicular to this magnetic field id deflected vertically, as explained above in reference to FIG. 2B.

Figure 3:
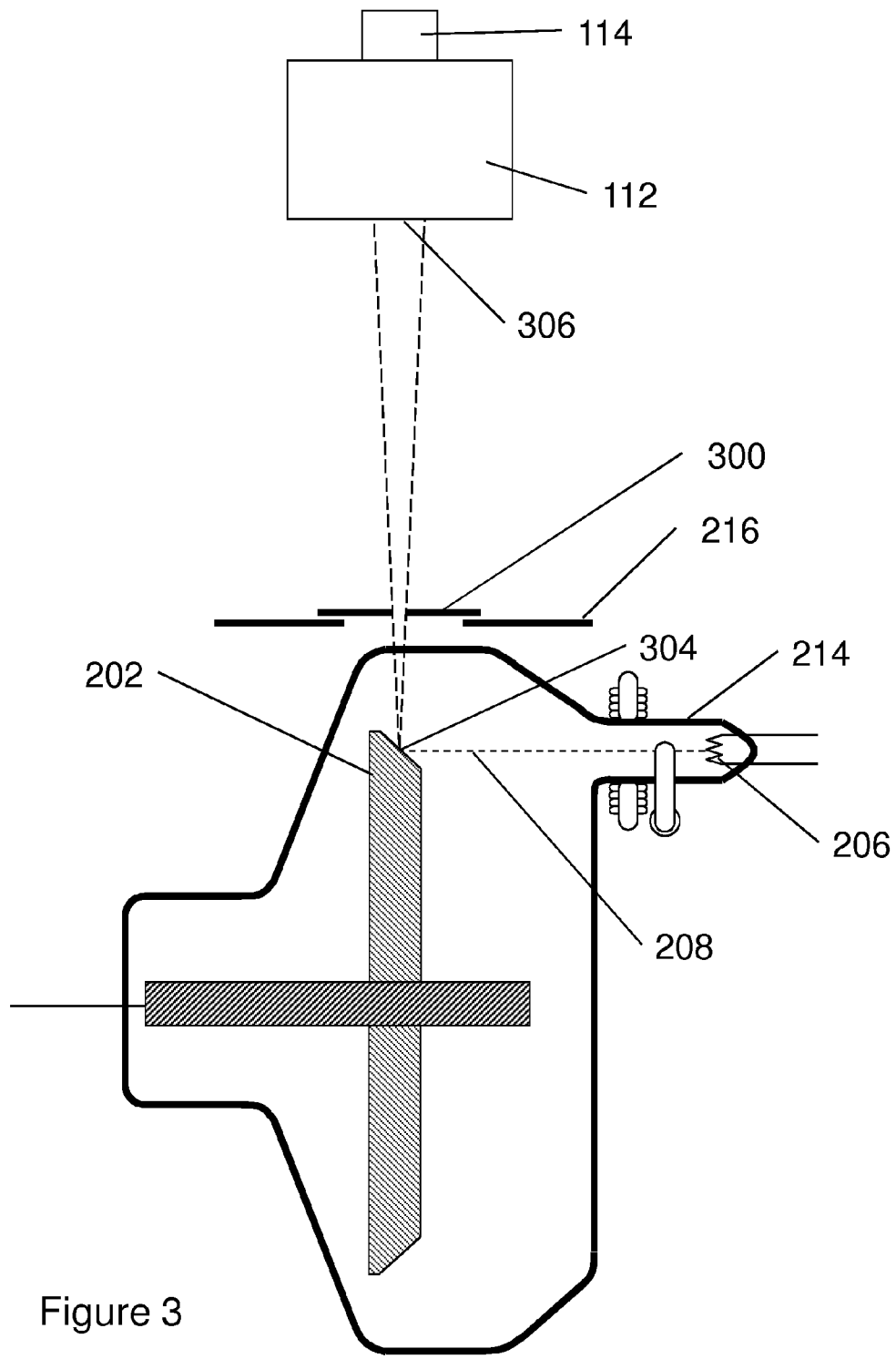
FIG. 3 illustrates an x-ray tube with a collimator configured to provide a relatively narrow cone of radiation at the center of the image intensifier input area.
Figure 4:
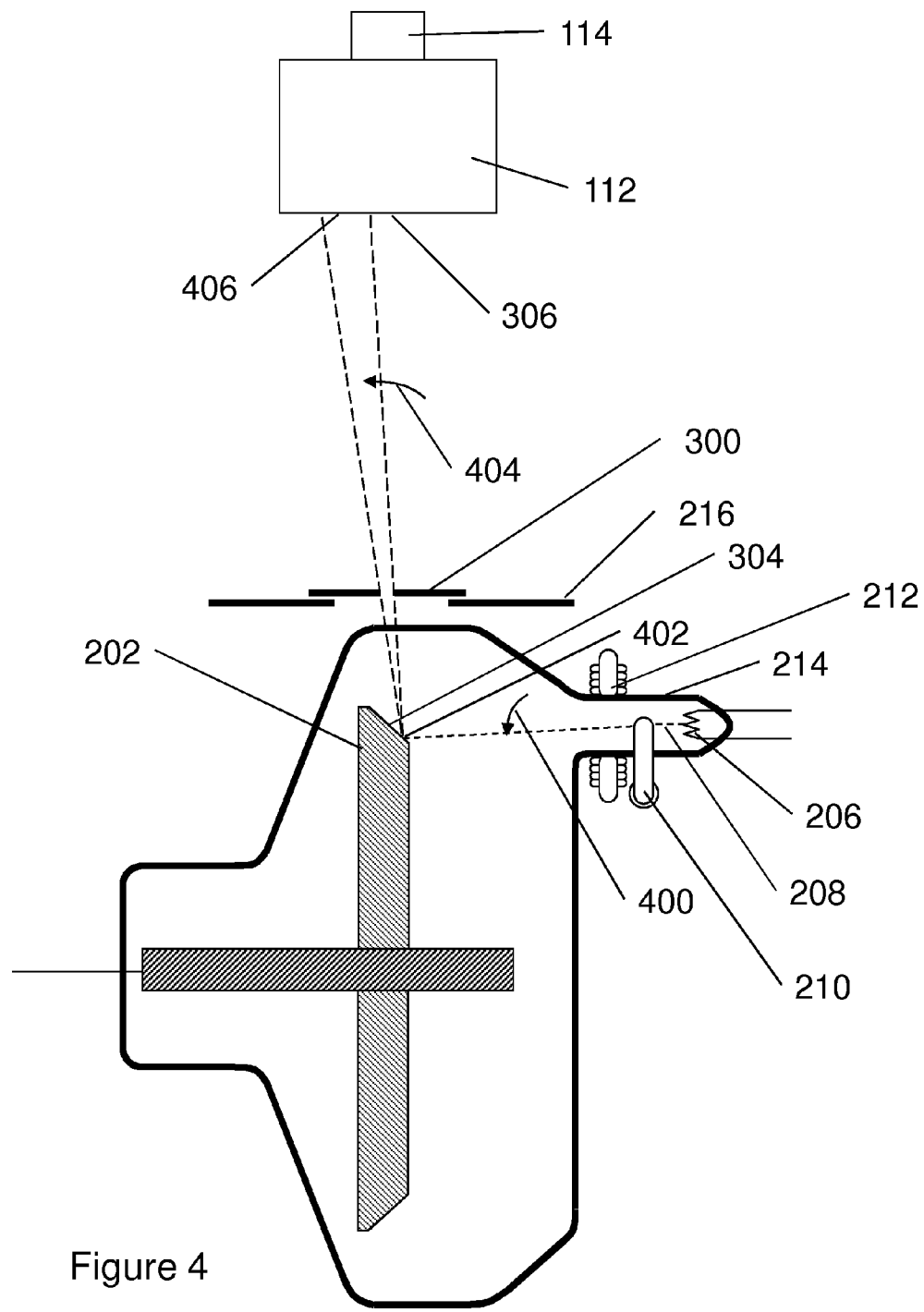
FIG. 4 illustrates the configuration of FIG. 3 with the electron beam deflected downwards and, as a result, the relatively narrow cone of radiation is deflected to the left side of the image intensifier input area.

FIG. 3 and FIG. 4 demonstrate how the x-ray tube of FIG. 2A and FIG. 2B is used to manipulate the direction of a relatively narrow x-ray beam.

Reference is made now to FIG. 3. In the example of FIG. 3 no current is flowing through the coils of yokes 210 and 212 and therefore electron beam 208 is not exposed to a magnetic field and hits the anode at point 304. A small aperture collimator 300 is placed in the beam way to reduce the solid angle of the x-ray beam. For example, a collimator with a round aperture of 5 mm placed at a distance d=75 mm above point 304 produces an exposure of 50 mm in diameter on the input area of image intensifier 112 when the input area is at a distance D=750 mm above point 304. Distances d, D and diameter (or other dimension for other aperture geometry) can be manipulated to get the desired geometry.

In the arrangement of FIG. 3, where no magnetic field is applied, the x-ray beam originating from point 304 of the anode 202 expose an area 50 mm in diameter centered about point 306 on the input area of image intensifier 112. For D=1000 mm and d=10 mm, a horizontal deflection of electron beam 208 of 1.5 mm will displace the exposure area 150 mm on the input area of the image intensifier. In such a case, to generate 50 mm diameter exposure on the input area of the image intensifier, the aperture in the collimator should be 0.5 mm in diameter.

Reference is made now to FIG. 4.

In FIG. 4, electrical current is driven through coil 209 (see FIG. 2B) that deflects the electron beam downwards as shown by arrow 400. As a result, the point where the electrons now hit the anode 202 has moved from position 304 of FIG. 3 to position 402. Due to the shift to the right in the point of origin of the x-ray beam, the whole beam direction rotates now anti-clock wise as shown by arrow 404 and the center of the exposure area in the input area of image intensifier 112 shifts from point 306 of FIG. 3 to point 406 of FIG. 4.

It would be appreciated by those skilled in the art that using this method, the narrow x-ray beam can by directed at any point on the input area of image intensifier 112. By controlling the currents in the coils of yokes 210 and 212 the 2-dimentional position of the exposure center (406 of FIG. 4 and 306 of FIG. 3 can be set to any desired position on the input area of the image intensifier.

By controlling the rate of change of the current in the coils, one can control the speed of motion of the exposure area though any desired path. The motion function (speed and location as a function of time) of the exposure area over the input area is fully controlled through the current in the coils of yokes 210 and 212. For example, driving yoke 210 and 212 using sine-wave function where yoke 212 sine-wave phase is delayed one π (180 degrees) relative to the sine-wave of yoke 210 will move the exposure area along an elliptic path on input area 112. The motion pattern can be designed to slow the x-ray beam in the specified ROI on input area 112 and move it faster over the rest of the input area thus getting a better exposure and a better image thereby in the ROI while reducing exposure and image quality elsewhere.

Figure 5A:
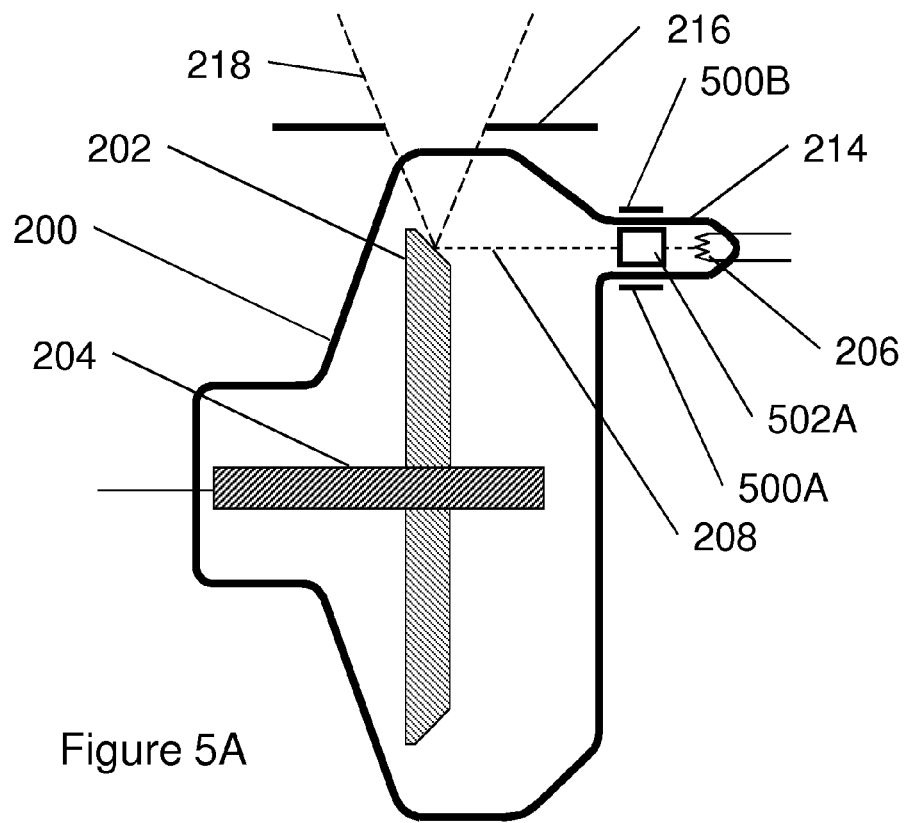
FIG. 5A illustrates a schematic x-ray tube with deflection plates.

Reference is made now to FIG. 5A.

Figure 5B:
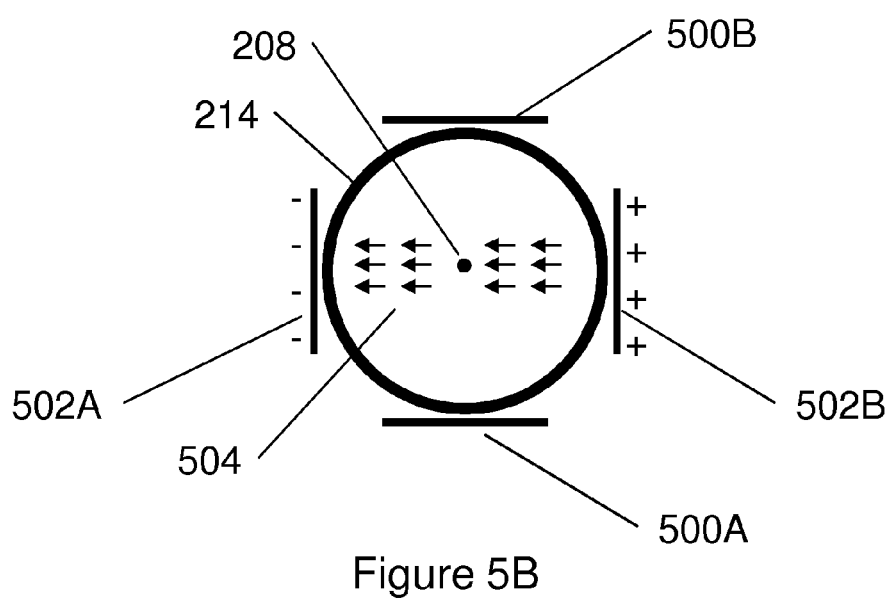
FIG. 5B illustrates a more detailed view of an arrangement of the deflection plates of FIG. 5A.

FIG. 5A illustrates construction of conductive plates instead of yokes for the deflection of electron beam 208. Plates 500A and 500B operate to deflect electron beam 208 in the vertical direction and plates 502A and 502B (only plate 502A is visible in FIG. 5A) operate to deflect electronic beam 208 in the horizontal direction. The deflection is better understood in reference to FIG. 5B. In the example of FIG. 5B, Left plate 502A is charged with a negative charge and right plate 502B is charged with a positive charge, inducing electrical field illustrated by arrows 504. As a result of this electrical field the electrons of electron beam 208 are deflected to the right. By using an opposite polarity on plates 502A and 502B electron beam 208 will be deflected to the left. Using plates 500A and 500B in the same way provides deflection of electron beam 208 in the vertical direction.

It would be appreciated that the magnitude of deflection of electron beam 208 is dependent on the potential difference between plates 500A and 500B and plates 502A and 502B.

It would also be appreciated that using only one plate for the horizontal deflection, such as plate 502A and charging it with positive or negative charge can also provide for the horizontal deflection of electron beam 208 and the x-ray tube can be constructed accordingly. The same holds for the vertical direction where only one of plates 500A or 500B can be used to vertically deflect electron beam 208.

Figure 6:
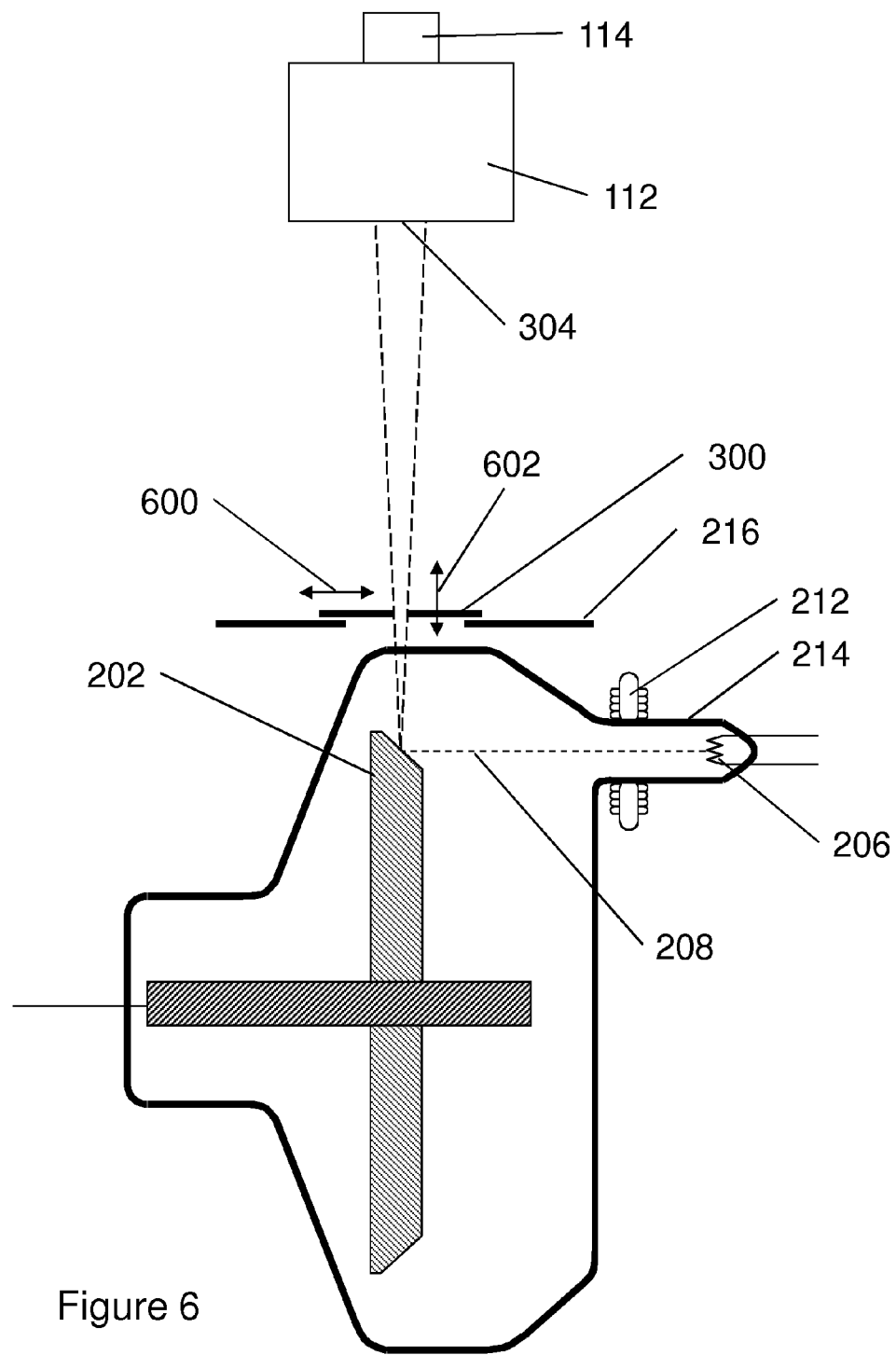

Reference is made now to FIG. 6.

In this example yoke 210 is removed and only yoke 212 is incorporated in the x-ray tube. With this assembly electron beam 208 can be deflected only horizontally, providing motion of the x-ray beam in direction perpendicular to the page. The other component of motion of the x-ray beam is provided here by the mechanical motion, preferably motorized, of collimator 300 in direction left/right as illustrated by arrow 600. By the combination of movements enabled by the yoke and in perpendicular direction by the movement of the collimator, the motion function of the exposed area can be fully controlled and support differential exposure in the ROI and outside the ROI.

By additionally enabling vertically controlled motion of collimator 300 as shown by arrow 602, the size of the exposed area, the radiation distribution over the exposure area and sensitivity of motion Vs control parameters can be modified. By moving collimator 300 upward the exposed area is reduced (the x-ray beam assumes smaller solid angle), the exposure area becomes more uniform and the sensitivity of position of the exposure area Vs electron beam deflection is reduced. These characteristics change in the opposite direction when collimator 300 is moved downwards.

A variable aperture collimator can be used to change the exposure area and it can also be used in combination with the above described vertical positioning of the collimator. This can enable, for example, moving the collimator upwards while increasing the aperture size to maintain the exposure area while changing the other parameters.

Figure 7:
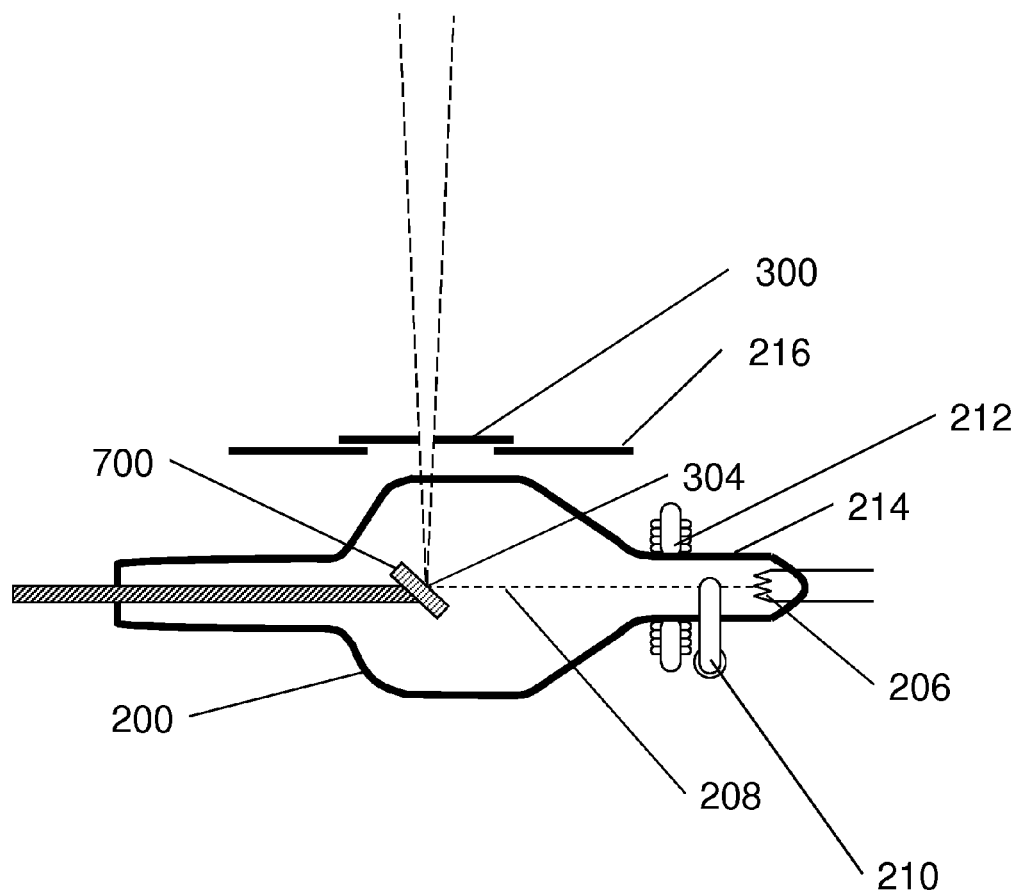
FIG. 7 illustrates an embodiment of the invention using a static-anode x-ray tube.

It would be appreciated that all the embodiments described above are not limited to rotating anode x-ray tubes and they can be implemented with static anode x-ray tubes without any difficulty. This option is illustrated in FIG. 7 where the static anode 700 is shown with the example of yokes 210 and 212.

To control the current of the yokes of the current invention, any controllable current source can be used. It is particularly convenient to use a digitally controlled current source to simplify the current manipulation using a computer or any other programmable device. An example for such a current source is MCP1631HV Digitally Controlled Programmable Current Source Reference Design by Microchip Technology Inc. Chandler, Ariz., USA.

It would be appreciated by those skilled in the art that the above described methods and technologies are not limited to the configurations and methods mentioned herein above. These are provided as examples and other configurations and methods can be used to optimize final result, depending on the specific design and the set of technologies implemented in the production of the design.

The herein above embodiments are described by way of example only and do not limit scope of the invention.

The scope of the invention is defined solely by the claims provided herein below and all equivalents:

The invention claimed is:

1. An x-ray system comprising:
an x-ray tube assembly;
a collimator forming an aperture;
an image detector;
a monitor configured to display detected images;
means for determining the location of a Region of Interest (ROI) of a patient on said displayed image;
a first controller connected with said means for determining the location of a ROI;
an image processing unit connected with said image detector, said monitor and said first controller, said image processing unit configured to modify the detected image for display on said monitor according to the image part in said ROI; and
a second controller connected with said x-ray tube assembly, said second controller configured to control operating parameters of said x-ray tube,
wherein said x-ray tube assembly comprises a cathode, an anode; and
means for controlling collision location of electrons emitted from said cathode on said anode in reference to said collimator aperture, configured to directing an emitted x-ray beam to said ROI;
said first controller configured to calculate a collision location of electrons emitted from said cathode on said anode according to said determined location of said ROI.

2. The x-ray system according to claim 1, wherein said means for determining the location of a ROI comprise an eye tracker.

3. The x-ray system according to claim 1, wherein said means for controlling collision location comprise two electromagnetic devices connected to a current source, said electromagnetic devices configured to produce magnetic fields in the path of electrons flowing from said cathode to said anode, said magnetic fields generally perpendicular to each other;
   wherein a current level is selected to generate a desired magnetic field in the path of electrons flowing from said cathode to said anode, and wherein a current in each of the electromagnetic devices is set to determine a collision location of the electrons emitted from the cathode on the anode.

4. The x-ray system according to claim 3, further comprising a collimator forming an aperture limiting a solid angle of an x-ray beam emitted from the x-ray tube;
   wherein the current in each of the electromagnetic devices is set to control a direction of said solid angle of the x-ray beam.

5. The x-ray system according to claim 4, wherein said aperture is movable in a plane generally parallel to a surface of the collimator.

6. The x-ray system according to claim 5, wherein a direction of said solid angle is determined by a combination of the current in each of the electromagnetic devices and the location of said movable aperture.

7. The x-ray system according to claim 5, wherein said first controller is further configured to calculate a location and size of said collimator aperture according to said determined location of the ROI.

8. The x-ray system according to claim 4,
   wherein said collimator is movable in a plane generally perpendicular to a surface of the collimator and
   wherein said first controller is further configured to calculate a location of said collimator aperture according to said determined location and size of the ROI.

9. The x-ray system according to claim 1, wherein said means for controlling a collision location comprise two devices for generating an electric field, said devices configured to produce electric fields in the path of the electrons flowing from said cathode to said anode, said electric fields generally perpendicular to each other, said devices connected to an electric potentials source, wherein electric potential levels are determined to generate a desired electric field in the path of electrons flowing from said cathode to said anode, and
   wherein the electric potential applied to each of the said devices is set to determine a collision location of electrons emitted from the cathode on the anode.

10. The x-ray system according to claim 9, further comprising a collimator forming an aperture limiting a solid angle of an x-ray beam emitted from the x-ray tube, wherein an electric potential applied to each of the devices is set to determine the direction of said solid angle of the x-ray beam.

11. The x-ray system according to claim 10, wherein said aperture is movable in a plane generally parallel to a surface of the collimator.

12. The x-ray system according to claim 11, wherein the direction of said solid angle is determined by a combination of the electric potential applied to each of said devices and a location of said movable aperture.

13. The x-ray system according to claim 10,
   wherein said collimator is movable in a plane generally perpendicular to a surface of the collimator, and
   wherein the direction of said solid angle is determined by a combination of the electric potential applied to each of said devices and the location of said movable aperture.

14. An x-ray system comprising:
   an x-ray tube assembly;
   a collimator forming an aperture;
   an image detector;
   a monitor configured to display detected images;
   means for determining the location of a Region of Interest (ROI) of a patient on said displayed image;
   a first controller connected with said means for determining the location of a ROI;
   an image processing unit connected with said image detector, said monitor and said first controller, said image processing unit configured to modify the detected image for display on said monitor according to the image part in said ROI;
   a second controller connected with said x-ray tube assembly, said second controller configured to control operating parameters of said x-ray tube; and
   a collimator forming an aperture limiting a solid angle of an x-ray beam emitted from said x-ray tube;
   wherein said x-ray tube assembly comprises a cathode, an anode; and
   means for controlling collision location of electrons emitted from said cathode on said anode in reference to said collimator aperture, configured to directing an emitted x-ray beam to said ROI;
   wherein said means for controlling collision location comprise two electromagnetic devices connected to a current source, said electromagnetic devices configured to produce magnetic fields in the path of electrons flowing from said cathode to said anode, said magnetic fields generally perpendicular to each other;
   wherein a current level is selected to generate a desired magnetic field in the path of electrons flowing from said cathode to said anode, and
   wherein a current in each of the electromagnetic devices is set to determine a collision location of the electrons emitted from the cathode on the anode; and
   wherein the current in each of the electromagnetic devices is set to control a direction of said solid angle of the x-ray beam.

15. The x-ray system according to claim 14, wherein said aperture is movable in a plane generally parallel to a surface of the collimator.

16. The x-ray system according to claim 15, wherein a direction of said solid angle is determined by a combination of the current in each of the electromagnetic devices and the location of said movable aperture.

17. The x-ray system according to claim 15, wherein said first controller is further configured to calculate a location and size of said collimator aperture according to said determined location of the ROI.

18. The x-ray system according to claim 14, wherein said collimator is movable in a plane generally perpendicular to a surface of the collimator; and
   wherein said first controller is further configured to calculate a location of said collimator aperture according to said determined location and size of the ROI.

19. An x-ray system comprising:
   an x-ray tube assembly;
   a collimator forming an aperture;
   an image detector;
   a monitor configured to display detected images;
   means for determining the location of a Region of Interest (ROI) of a patient on said displayed image;
   a first controller connected with said means for determining the location of a ROI;

an image processing unit connected with said image detector, said monitor and said first controller, said image processing unit configured to modify the detected image for display on said monitor according to the image part in said ROI; and a second controller connected with said x-ray tube assembly, said second controller configured to control operating parameters of said x-ray tube, wherein said x-ray tube assembly comprises a cathode, an anode; and means for controlling collision location of electrons emitted from said cathode on said anode in reference to said collimator aperture, configured to directing an emitted x-ray beam to said ROI;

wherein said means for controlling a collision location comprise two devices for generating an electric field, said devices configured to produce electric fields in the path of the electrons flowing from said cathode to said anode, said electric fields generally perpendicular to each other, said devices connected to an electric potentials source, wherein electric potential levels are determined to generate a desired electric field in the path of electrons flowing from said cathode to said anode; and wherein the electric potential applied to each of the said devices is set to determine a collision location of electrons emitted from the cathode on the anode.

20. The x-ray system according to claim 19, further comprising a collimator forming an aperture limiting a solid angle of an x-ray beam emitted from the x-ray tube, wherein an electric potential applied to each of the devices is set to determine the direction of said solid angle of the x-ray beam.

21. The x-ray system according to claim 20, wherein said aperture is movable in a plane generally parallel to a surface of the collimator.

22. The x-ray system according to claim 21, wherein the direction of said solid angle is determined by a combination of the electric potential applied to each of said devices and a location of said movable aperture.

23. The x-ray system according to claim 20, wherein said collimator is movable in a plane generally perpendicular to a surface of the collimator, and wherein the direction of said solid angle is determined by a combination of the electric potential applied to each of said devices and the location of said movable aperture.

* * * * *